United States Patent [19]

Becker

[11] Patent Number: 4,528,265
[45] Date of Patent: Jul. 9, 1985

[54] PROCESSES AND PRODUCTS INVOLVING CELL MODIFICATION

[76] Inventor: Robert O. Becker, Erie Canal Rd., Star Rte., Lowville, N.Y. 13367

[21] Appl. No.: 377,038

[22] Filed: May 11, 1982

[51] Int. Cl.³ .................. C12N 15/00; C12N 1/36; C12N 13/00; C12N 5/00

[52] U.S. Cl. ................... 435/172.1; 435/245; 435/240; 435/173; 424/132; 604/20; 128/419 R; 128/419 F

[58] Field of Search .......... 435/173, 172, 240, 241, 435/948, 245; 424/131, 132; 128/419 R, 419 F; 604/20, 21

[56] References Cited

U.S. PATENT DOCUMENTS

| | | | |
|---|---|---|---|
| 2,121,875 | 6/1938 | Fischer et al. | 204/24 |
| 2,355,231 | 8/1944 | Moore | 128/172.1 |
| 3,035,968 | 5/1962 | Degoli | 167/14 |
| 3,337,405 | 8/1967 | Lacharme et al. | 167/60 |
| 3,893,462 | 7/1975 | Manning | 128/421 |
| 3,918,459 | 11/1975 | Horn | 128/419 R |
| 3,964,477 | 6/1976 | Ellis et al. | 128/172.1 |
| 4,019,510 | 4/1977 | Ellis | 128/172.1 |
| 4,027,393 | 6/1977 | Ellis et al. | 32/10 |
| 4,126,937 | 11/1978 | Ellis et al. | 32/15 |
| 4,177,263 | 12/1979 | Rosenberg et al. | 424/131 |
| 4,291,125 | 9/1981 | Greatbatch | 435/240 |
| 4,313,438 | 2/1982 | Greatbatch | 128/419 F |
| 4,314,554 | 2/1982 | Greatbatch | 128/419 F |

FOREIGN PATENT DOCUMENTS 3222202 2/1972 U.S.S.R.

OTHER PUBLICATIONS

Marino, A. A. et al., "The Effect of Selected Metals on Marrow Cells in Culture"; Chem.-Biol. Interactions 9, 217-223, 1974.
Spadaro, J. A. et al., "Antibacterial Effects of Silver Electrodes with Weak Direct Current", Antimicrob. Agents & Chemo. 6, 637-642, 1974.
Spadaro, J. A. & Becker, R. O., "Treatment of Localized Infections with Electrochemically Injected Silver"; Proc. 22nd Ann. Meet. Ortho. Res. Society, 1976.
Berger, T. J. et al., "Electrically Generated Silver Ions: Quantitative Effects on Bacterial & Mammalian Cells"; Antimicrob. Agents & Chemo. 9, 357-358, 1976.
Berger, T. J. et al., "Antifungal Properties of Electrically Generated Metallic Ions"; Antimicrob. Agents & Chemotherapy 10, 856-860, 1976.
Yuan, H. et al., "Electrically Generated Silver Ions as a Bactericidal Agent in Acute & Chronic Enterobacterocloacae Osteomyelitis in Rabbits", Proc. 23rd Ann. Meet. Ortho. Res. Soc., 1977.
Spadaro, J. A. et al., "Antitumor Effect of Silver Electrodes in Vitro", Proc. 3rd Ann. Biomaterials Meet., 1977.
Becker, R. O. & Spadaro, J. A., "Treatment of Orthopaedic Infections with Electrically Generated Silver Ions," J. Bone & Joint Surg. 60-A, 871-881, 1978.
Spadaro, J. A. & Becker, R. O., "Experience with Anodic Silver in the Treatment of Osteomyelitis"; Proc. 25th Ann. Meet. Ortho. Res. Soc., 1979.
Webster, D. A. et al., "Silver Anode Treatment of Chronic Osteomyelitis"; Clin. Ortho. & Rel. Res. 161, 105-114, 1981.
Becker, R. O. & Spadaro, J. A., "Experience with Low Current/Silver Electrode Treatment of Non-Union"; in Electrical Properties of Bone and Cartilage, ed. Brighton, C. T., Black, J., and Pollack, S. R., Grune and Stratton, 1979.
Becker, R. O., "Electrostimulation and Undetected Malignant Tumors"; Clin. Ortho. & Rel. Res. 161, 336-339, 1981.

Primary Examiner—Lionel M. Shapiro
Assistant Examiner—J. Tarcza
Attorney, Agent, or Firm—Kenyon & Kenyon

[57] ABSTRACT

Living mammalian cells are modified by subjecting them to the influence of the ions from a metal electrode, for example of silver, which is placed in contact with them and which is made electrically positive, and causing a low intensity direct current to flow through them. The cells, which are relatively specialized, such as normal mammalian fibroblasts, assume a simpler, relatively unspecialized form and come to resemble hematopoetic or marrow-like cells.

24 Claims, 13 Drawing Figures

EDGE OF EXPLANT

ROUND CELLS PRODUCED.

1 WEEK     2 WEEKS     3 WEEKS

GRANULATION TISSUE CULTURE PRODUCING ROUND CELLS.

ORIGINAL GRANULATION TISSUE FRAGMENT REMOVED AND PLACED IN NEW CULTURE.

ROUND CELLS LEFT BEHIND. CULTURE MEDIA CHANGED.

2 WEEKS          2 WEEKS

CONVERSION BACK TO FIBROBLASTS.

PRODUCTION OF FIBROBLASTS ONLY.

PROCESSES AND PRODUCTS INVOLVING CELL MODIFICATION

This invention relates to cells, especially mammalian cells, and provides novel cell modifying processes and pharmacological agents for producing novel modified cells and cell cultures, and for providing novel and/or improved biological, pharamcological and/or therapeutic effects, such as enhanced cell or biochemical production, enhanced lesion healing, enhanced normal tissue growth or regeneration, cell dedifferentiation, changing cancer cell form, and stopping multiplication of cancer cells.

BACKGROUND OF THE INVENTION

It has been heretofore proposed to modify living cells so as to obtain cells differing in function or biochemical output. Thus, normal cells have been changed to cancerous cells by exposure to mutagenic influences. For the production of useful biochemicals or the enhancement thereof, normal cells have been hybridized with malignant cells or altered in genetic makeup by the insertion of viral material.

Metal ions have been applied to cells, as for instance, silver, associated with various anions or anion complexes, or free of anions. However, except for Netien et al., U.S. Pat. No. 3,337,405, which teaches a therapeutic effect on tissue for complexed silver ion, and Mironenko et al., U.S.S.R. Author's Certificate No. 322,202, which teaches an unspecified therapeutic effect of silver ions from silver salts on certain viscera, application of silver ions to cells or tissue, for treatment or pharmacological purposes, has been for the purpose of disinfection. Aside from natural processes, such as cell metabolism in which certain metal ions play a part, metal ions are generally considered to fall into the categories of inert, toxic, and mutagenic, with respect to cells. Silver as such, aside from cosmetic effects, is now generally regarded as inert, or at least harmless insofar as human tissue is concerned. The use of silver ions against bacterial infections is described in "Silver Anode Treatment of Chronic Osteomyelitis" by D. A. Webster et al., Clinical Orthopedics and Related Research, Number 161, November-December, 1981, pp. 105–114 and in "Treatment of Orthopedic Infections With Electrically Generated Silver Ions" by R. O. Becker et al., Journal of Bone and Joint Surgery, vol. 60-A, No. 7, October 1978, pp.871–881.

In testing the use of silver ions against bacterial infections in chronic osteomyelitis, a silver nylon electrode, in contact with the wound, was made electrically positive with respect to the surrounding tissue of the patient. Passage of a low level direct current through the electrode for a period of three hours per day, with normal wound care for the reset of the time, resulted in a satisfactory drop in bacterial counts. To distinguish between the effect of the wound treatment, since it might be the effective agent rather than silver, I began treating for twenty-four hours a day. Results with a few patients seemed to be the same, so I went to twenty hours a day. This resulted in an enhancement of the effect against bacteria, the appearance of an exudate, and markedly increased rates in wound healing. Subsequent analysis has shown that an heretofore unappreciated effect is produced by the application of current for an extended period of time by which the silver promoted both a cell modification akin to dedifferentiation and mitotic activity.

SUMMARY OF THE INVENTION

According to the present invention, suitable metal ions from a positive electrode are applied to living mammalian cells in order to modify them. For example, under the influence of positive silver ions, normal mammalian fibroblasts, which are relatively specialized cells, first assume a simpler, relatively unspecialized form, and then, still under said influence, come to resemble hematopoietic or marrow-like cells. The relatively unspecialized cells, if cultured in vitro in the absence of the silver ions, become normal fibroblasts again.

In vitro, normal mammalian fibroblasts are cultured on either a glass surface or on a collagen surface. In the latter case, there is a greater yield of the unspecialized form, than in the former case.

If the positive silver ions are applied in vivo to a mammalian lesion, or continue to be applied to an in vitro explant of granulation tissue from that lesion, the same thing occurs to the fibroblasts except that, in the in vivo case, applying the silver ions also enhances and accelerates healing of the lesion.

If the positive silver ions are applied to cancerous cells, for example, saracomatous fibroblasts, these, too, change to simpler form resembling the relatively unspecialized or multipotent form which results from modifying normal fibroblasts by applying the positive silver ions thereto, and, like the modified normal fibroblasts, revert to their original malignant form if cultured in vitro in the absence of the silver ion. Further, the cells do not proliferate while in the modified form.

The relatively unspecialized cells can be frozen and stored. Prior to the present application for U.S. Letters Patent, I have made an exemplary deposit thereof in the American Type Culture Collection, an internationally recognized depository for microorganisms, said deposit having been assigned the Deposit Number SD427.

In one form of the invention, I locate an element of silver metal at a culture medium having relatively specialized cells therein, and provide a source of low intensity direct current, of which the anode is connected to the element, and the cathode to the medium. As a result, anodal (i.e., positive) silver ions, free of or unassociated with any anions, travel through the medium, contact cells therein and change them to relatively unspecialized form. In this form of the invention, I prefer to culture cells (in accordance with prior art technique) on a suitable surface, e.g., either that of a glass cover slip, or that of a collagen coating on a glass cover slip, and then to apply the silver ions to the resulting cell culture.

In another form of the invention, the cells to be modified are provided in the form of an explant of granulation tissue such as normally develops in a lesion as part of the natural healing process.

In still another form of the invention, a silver nylon mesh electrode is placed in contact with the surface of a lesion in vivo and then connected to the anode of a source of low intensity direct current, of which the cathode contacts tissue adjacent the lesion. In this way, the material in the lesion provides a medium containing cells, fibroblasts in particular, some of which the silver ions contact and change to relatively unspecialized form. The modified cells then seem to initiate or enhance or accelerate the natural healing process wherein healthy tissue is caused to form, integral with the tissue around the lesion; e.g. they form the basis for new tissue. In the course of this process, the lesion develops much more than the usual granulation tissue which may be used as source of explants for the production of modified cells elsewhere, either in vivo or in vitro.

The modified cells from the explants can then be allowed, or caused, to partly or wholly respecialize to original form (e.g., fibroblast) or to a different form (e.g., hematopoietic or marrow-like).

The modified cells can also be frozen and stored for later use, either for application to the individual who was the source of cells subjected to modification, or for later study, testing or experiment.

I believe that cell modification or change as described above is dedifferentiation to a multipotent state, and that the cells have the potential of being induced to redifferentiate along an arbitrarily chosen pathway leading to a specialized form other than the one they had prior to dedifferentiation. In this, there is the potential for regeneration of various tissues, and organizations thereof such as organs, limbs and the like. Again there is the potential for dedifferentiating cells of one kind, and causing them to redifferentiate as cells of another kind having useful biochemical capabilities superior to or different from those of the original cells. Finally, dedifferentiation offers the potential of dedifferentiating cells to the extent of creating cells in which the all the genetic potential of the source can be expressed in a true clone.

While I am unable to state flatly that I have achieved dedifferentiation of cells to a fully totipotent state, in my laboratory, nevertheless, the nucleated red blood cell of the frog has been shown to be the cell or origin of fracture blastema (frog red blood cells dedifferentiating to primitive state and redifferentiating as frog bone at fracture sites in the frog.) Likewise, it was shown that the same kind of red blood cell regenerates salamander heart (salamander red blood cells dedifferentiating to primitive state and redifferentiating to salamander myocardium). Again, it is known that fibroblasts, through contact with properly prepared bone matrix, are thereby induced to become osteoblasts and form bone.

It is clear, therefore, that cell modification, or dedifferentiation, in accordance with my invention, provides a useful tool for studying the creation of multipotency, and the potentials of multipotency, cell transformation, lesion repair or healing, tissue-regenerative processes, cell proliferation, tumor-regression, and the like.

In any event, I have used my novel discoveries, not only to produce the relatively unspecialized cells, but also to heal refractory lesions of human sufferers of longstanding osteomyelitis, to stimulate bone growth and to enhance healing of the soft tissues.

DETAILED DESCRIPTION OF THE INVENTION

Figure 1:
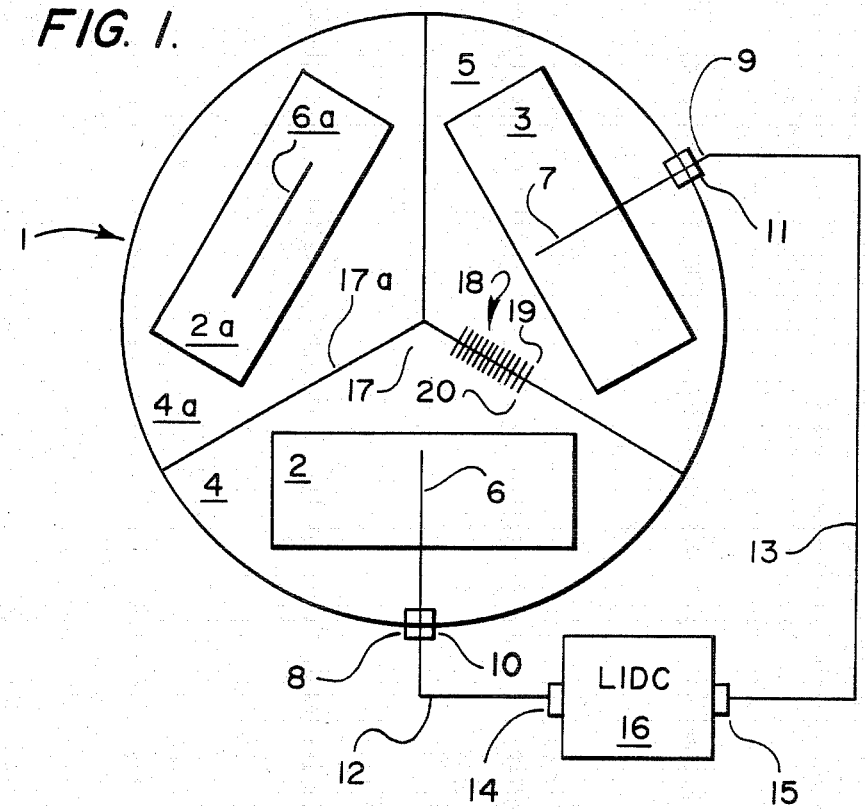
FIG. 1 shows apparatus for exposing living cells to anodal metal ions in vitro, in accordance with the invention.

In FIG. 1, a triwell culture dish 1, preferably of transparent plastic or glass, has microscope-type thin glass cover slips 2, 2a and 3 in the bottoms of chambers 4, 4a and 5. Slips 2, 2a and 3 are biologically inert substrates upon which to grow cells, but can be omitted if the triwell is glass because the glass surface in the triwell would be a satisfactory substrate.

In chambers 4 and 5 are respective electrodes 6 and 7 consisting of 20 AWG, 99.99 fine, silver wire. The respective electrode lead ends 8 and 9 pass through holes (not shown) in the chamber walls, are hermetically fixed in place by respective cement plugs 10 and 11, which fill and seal such holes and are placed in contact with the culture. A suitable cement is medical grade silicone rubber or epoxy. In chamber 4a, which serves as an electrically passive control chamber, a silver wire 6a is placed.

The electrode leads 12 and 13 are connected to terminals 14 and 15, respectively, of a low intensity direct current generator 16. Generator 16 is capable of driving 360 to 400 nA of electrical direct current through a culture medium in dish 1. Generator 16 may well be a commercially-available generator, such as Sybron Corporation's VITRON LIDC generator.

In order for the aforesaid direct current to transverse a divider 17 separating the contents of chamber 4 from the contents of chamber 5, a bridge 18 is provided. Bridge 18 consists essentially of electrically conductive material, non-reactive with respect to the contents of chambers 4 and 5, and, in particular, non-toxic with respect to cells therein. Bridge 18 is draped over, or mounted in an aperture (not shown) in, the divider, and has portions 19 and 20 in and making electrical contact with the medium or media (not shown) in respective chambers 5 and 4. The bridge can be normal saline solution in agar gel.

In use of this apparatus, all suitable precautions are taken to prevent contamination of medium therein by undesired life-forms. Before use, for example, it is sterilized by ethylene oxide, outgassed, and then stored for two weeks, before filling with medium. Again, once a culture is in place therein and being incubated, the dish 1 will not only have a sterile cover (not shown) thereon, but preferably also will be enclosed within a second sterile enclosure within the incubator. From beginning to end of such use, all necessary precautions will be taken, when manipulating the apparatus, to prevent contamination of the medium. While extreme ambient conditions are to be avoided, and all precautions should be taken which are usual to the art of cell culture, it appears that processes according to the present invention are not significantly influenced by room illumination, whether daylight or artificial light, and that incubation temperatures, room temperature and other ambient conditions, culture media, etc., used therein, are not other than the choices expectable of one of ordinary skill in the art of cell culture, supposing that such person were also possessed of the basic concept of my invention, as disclosed and claimed herein.

Unless otherwise indicated, the foregoing practices, expedients, and philosophy, apply to all the in vitro examples of my invention, now to be described.

EXAMPLE I

Modifying 3T6 mouse fibroblasts. Chambers 4 and 5 are each charged with a solution of Delbecco's modified Eagle's medium with Hepe's buffer and 10% fetal bovine serum. Bridge 18 is provided in the form of "brain-heart infusion" agar, and one or both of chambers 4 and 5 are seeded with 3T6 from American Type Culture Collection (ATCC), 12301 Parklawn Drive, Rockville, Md. 20852. If only one chamber is seeded, say chamber 5, terminal 15 would be the anode of generator 16. If, then, chamber 4 is also seeded, its electrode will act as cathode, (i.e., terminal 14 is the negative terminal of generator 16), and won't cause any changes in the cells which can be ascribed to the positive silver ion treatment. Hence, chamber 4 provides a means of control by which to judge whether the cell modification process, etc., are proceeding properly.

The third chamber 4a of the triwell 1, as stated above, can be fitted as a passive control. Thus, a silver wire 6a, a cover glass 2a, and a culture and medium could be provided in chamber 4a and subjected to the culturing and incubating procedure to be desired, infra. No electricity is applied in chamber 4a, however.

Using 3T6 Swiss Albino mouse fibroblasts (for a description of these cells see ATCC, Catalogue of Strains II, Third Edition, 1981, page 88, item ATCC CCL 96), and incubating them for 72 hours at 37° C., then, as a result of normal development processes, the cells triple in number (in each chamber, supposing that all are seeded). Although there is abundant growth of fibroblasts at the end of this time, the surface of slip 3 is not completely covered, but it is at this incompletely-covered stage that observations of individual cell changes are easiest to interpret. No electricity is applied to the cells during these 72 hours, so the tripling is due to mitosis. At this point, then, the low intensity current generator is attached to the electrode leads and the dish 1 is incubated as before but for 24 hours only and with 360-400 nA current being passed therethrough continuously by generator 16 during that time, at about 0.3 v.

It is during this last twenty-four hours that the cells change and, moreover, float free in the culture medium. Prior to the electrification, the normal cells were firmly attached to the cover glass slip. Thus, supposing that electrode 7 was the anode, it now results that floating, modified cells can be picked up by pipette from the medium in chamber 5, whereas there will be no change and no floating cells in chambers 4 or 4a.

In the operation of the apparatus of FIG. 1, significant changes are observed only at the anode electrode and only when a suitable anode material, e.g., metallic silver, is used. These changes are time dependent and spread out geographically from the anode in a roughly linear fashion. Cell changes go to completion in a zone 5-10 mm. around the anode with six hours of treatment in the incubator, but require longer times if treated at room temperature. If cultures treated for six hours are replaced into the incubator for twelve hours with the current turned off, all of the cells in the anode chamber will undergo the same kind of changes as did those in the 8-10 mm anode zone in the first six hours, presumably from the effect of the silver ion still remaining in the medium in chamber 5.

The changes are best described from the state of the cells observed, at the end of the initial six hour current treatment, by phase contrast microscopy.

Figure 2:
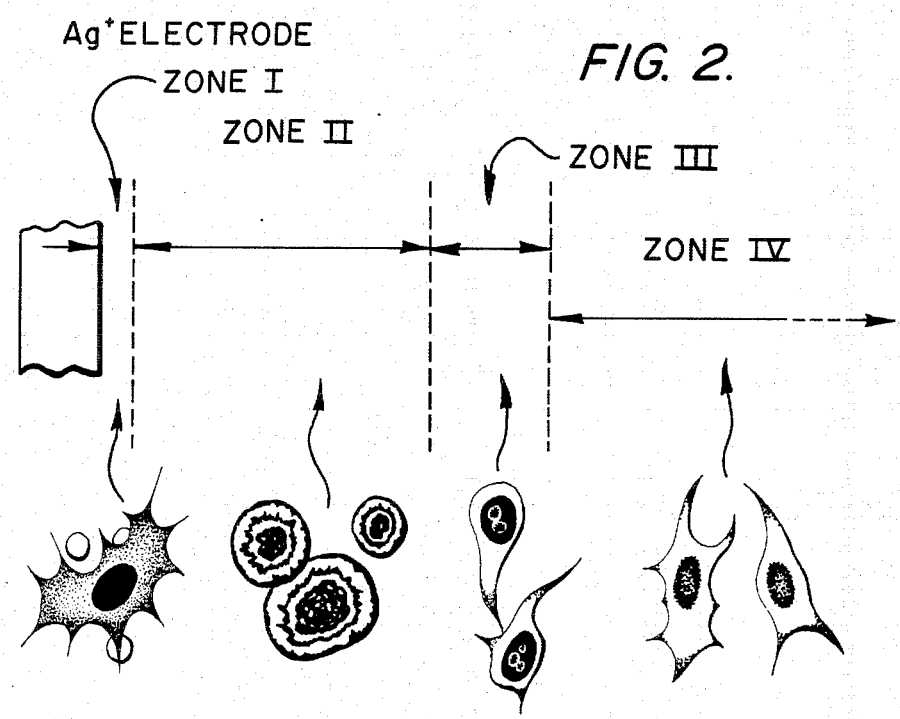
FIG. 2 shows the effects of one mode of operation of the FIG. 1 apparatus on living cells, in accordance with the invention, FIGS. 3, 4, and 5 being phase contrast microphotographs of live cell structure corresponding to zones I, II and III, respectively, FIG. 2.

As FIG. 2 shows, a first zone, I, extends from directly beneath the electrode 7 out for 1 mm from the electrode and along the length of the slip 3. (N.B. The shapes and relative positions of slip 3 and electrode 7 are as shown in FIG. 1). Shortly after current is turned on, the cells in zone I become very active, demonstrating many filapodia (thin projections from the previously smooth cell membrane), the cytoplasm becoming granular and the nucleus becoming very distinctly visible. After some additional treatment time, areas of change of state of the cytoplasm appear directly beneath the cell membrane. These migrate through the membrane and appear as round "blebs" or vesicles giving a ground glass appearance to the exteriors of the cells. Total cell volume diminishes somewhat, but the cells remain extended and maintain adherence to the glass regardless of the time of current administration.

Contemporaneously, a second zone II, 1 mm out from the electrode, extends to a boundary 5-10 mm out from the electrode. Initially the cells in this zone demonstrate the same changes as noted in zone I, but bleb formation is more evident and accelerates with marked diminution in cell volume. Increase in the size of the nucleus with appearance of nucleoli accompanies this and the cells become round in contour and lose adhesion to the glass substrate. In about 24 hours, when the transformation is complete, the phase contrast picture is one of round cells of various sizes floating in the media, some free and some in clumps. If the electrode is raised 5 mm above the culture, changes similar to the clumps in zone II would be seen under the electrode.

A third zone, III, extends from the outer boundary of zone II for an additional 3-4 mm into the culture. Cell changes are similar to and contemporaneous with those in zone II, but less in amount. While the filapodia formations are less in number, as compared to zone I, the filapodia of zone III are larger and longer and have a marked tendency to contact adjacent cells, forming a "network" of interconnected cells. These cells do not lose adhesion to the glass substrate.

A fourth zone, IV, is the remainder of the culture outside of zone III, and remains essentially unchanged, i.e., has the original 3T6 morphology. However, frequently loose clumps of cells from zone II will either migrate or be mechanically displaced into zone IV.

It is possible to follow a single cell sequentially through most of the changes in zone II, by phase contrast microscopy. Utilizing a projection technique, the outlines of these cells can be determined as they progress through the change sequence. This techniques reveals that a real diminution in cell volume occurs, and that the filapodia formation is an active event, rather than, say, an artifact of shrinkage. Thus, photographic FIGS. 3, 4 and 5, by phase contrast and under equal magnification, show contemporaneous living cells of zones I, II and III, respectively, after about 24 hours of treatment of the culture from which the cells were taken.

Stained slides reveal the true extent of the cell changes observed by the phase contrast microscopy. All of the cells in zones I through III show marked signs of activation. The transformed cells floating free are usually round, as in zone II, having basophilic cytoplasm, large nuclei and abundant nucleoli and contain azurophilic granules. Clumping, however, as in the FIG. 4 version of zone Ii, appears to stimulate differentiation, for the clumped round cells develop a pleomorphic appearance. Thus, many of the clumped cells now present the appearance of primitive cells of the white blood cell series, promyelocytes of various stages. Other resemble lymphoblasts, Turck cells, immature lymphocytes and monocytes. Morphologically, except that cells resembling mature while cells and megakaryocyte cells appear to be absent, the clumped transformed cell population comes to resemble that seen in bone marrow.

Left to themselves, floating freely in silver-free medium, the round cells do not reproduce but eventually revert to their original fibroblast form, if cultured in the absence of silver. Clumping, however, apparently induces them to differentiate toward a hematopoietic-like state. From this, I believe, it may well be concluded that the round cells are basic, primitive, mesenchymal cells, which need only the appropriate inducing signal or stimulus to start them differentiating in a direction or directions determined by the inducer.

As to identification of the hematopoietic-like cells, in actual practice, as is well-known, cells of bone marrow smears are reliably only if it is known beforehand that they have been obtained from the bone marrow, and have certain morphological characteristics. (There are frequentely cells in clinically normal bone marrow smears that cannot be identified with precision.)

One characteristic of the most primitive marrow cell, of all series, is the presence of azurophilic granules in the cytoplasm. Almost all of the cells of zones I and II, and a majority of zone III, contain these granules.

There is a difference of appearance between the stained preparations obtained from the cultures exposed to the electrically generated silver ion while in the incubator at normal body temperature, compared to those exposed to electrically generated silver ion while kept at room temperature. While the picture obtained from room temperature experiments also resembles bone marrow, it is not typical because the cell are scattered, the clumps are small and frequently cell types are seen that appear to be incompletely changed and poorly stained.

Silver anode treatment is known by clinical observation to be growth stimulating, so the effect of the ion treatment probably begins as soon as current flows through the medium. However the initial flow of positive silver ion, at least, is probably taken up largely by the medium, and hence is not immediately available to effect the fibroblasts.

Thus, phase contrast microscopy, only after about a first, apparently, uneventful, minute of silver ion treatment and incubation, shows cells developing ruffled borders on the sides facing electrode 7, 50% reduction of nuclei sizes, and granular cytoplasm, which effects, I believe, are due to the silver ion. After fifteen minutes, blebs or vesicles form immediately under the cell membrane, exiting the cells after about one hour, and cell processes that have been at 90° to current flow become thin and nodular.

The dramatic changes induced by the silver ion are, so far, not well understood. For example, it is not known what factor or factors determine the type of cell to be derived from any single fibroblast. Not surprisingly, perhaps, the final cell population is not uniform and at least six different types can be seen, probably because it was derived from a non-uniform cell population to begin with.

If normal bone marrow cells are placed in a standard culture medium, it is known that they will not retain their characteristics, but will, within a short time (one week), revert to a pure culture of fibroblasts. This happens presumably because they are no longer in the bone marrow cavity and are not receiving appropriate instructions to remain as bone marrow cells. However, the relatively unspecialized condition indefinitely, i.e., prevented from reverting to fibroblasts with further culturing. Since zone II cells are not adherent to cover glass, they can be pipetted off, sedimented down and explanted into other culture dishes. If the culture media contains electrically generated silver ions, it appears that they can retain their rounded form indefinitely. If the media is silver free, however, they will revert to 100% fibroblasts by one week. Therefore, the changes caused by my invention are permanent, in effect, in the presence of silver ion.

To test for viability and stability of the transformation, samples of the transformed cells were frozen, stored for several days, and thawed. Immediately after thawing, the cells proved viable as determined by subjecting them to the Trypan Blue exclusion test, and they remained viable and in the transformed state for the next several days in culture. Other thawed samples, not involved in exclusion testing, were incubated for 7 to 10 days (in the absence of silver ions) without degenerating, and eventually returned to normal fibroblast configuration.

Example II.

Figure 3:
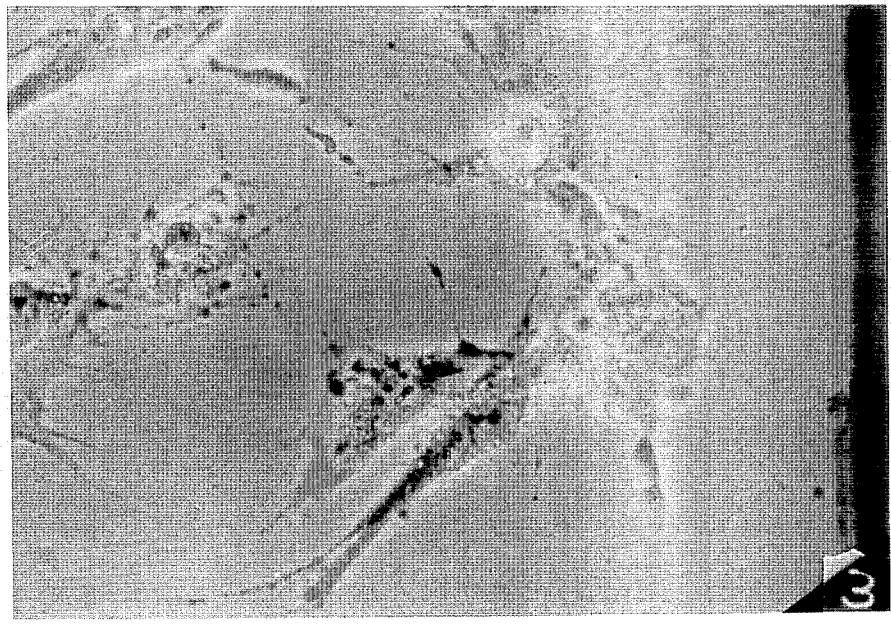
Figure 4:
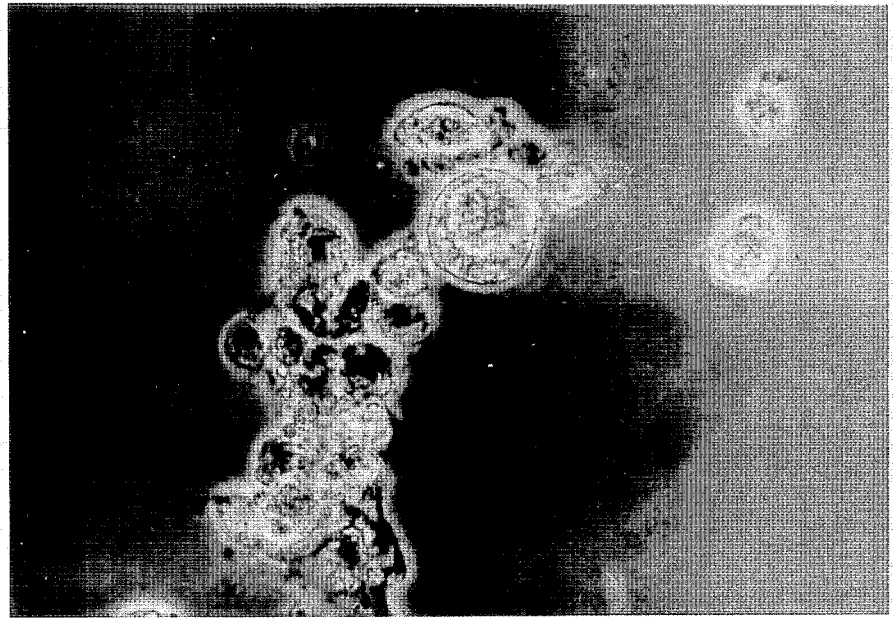
Figure 5:
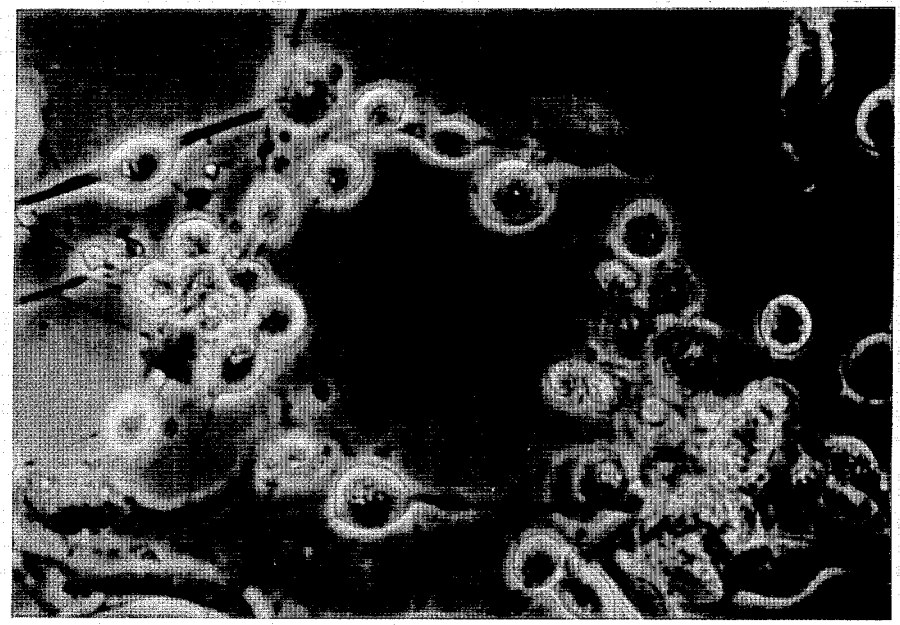

Substantially the same as in Example I, except that the cover slips are coated with collagen and the fibroblasts are cultured directly on the collagen substrate, thus provided (in Example I, the fibroblasts are cultured directly on a substrate in the form of the glass surfaces of the cover slips). In this example, substantially all the changed cells of Zone II are small and round. Otherwise, on the whole, FIG. 2 applies to Example II, insofar as chamber zones and cell-morphology are concerned, and FIGS. 3, 4 and 5 are the same. In particular, from the foregoing Example II with ATCC CCL 96 3T6-Swiss Albino mouse cells, I have obtained ATCC Deposit Number SD427.

The modified cell-type of Examples I and II is distinguished from ATCC CCL 96, as follows:

(a) By microscopic inspection, the modified cells differ from 3T6 cells in that they are round, free floating, basophilic cytoplasm having prominent nucleoli.

(b) The modified cells are remarkably fragile (as is typical of primitive cell types). Fragility is shown by the fact that mild centrifugation of Example I modified cells produces cell rupture.

EXAMPLE III

Modifying normal human fibroblasts (ATCC's CCL 186, IMR-90). The modification procedure is generally as in Example I, supra. As is known, all human cells grow at a slow rate and this was the general experience with modification of these older cells using the procedure of example I. Also, in a special test, some of these IMR-80 fibroblasts were allowed to undergo some 10 cycles of mitosis, which as is known, slows down normal growth rate. Expectably, therefore, the yield of the silver anode process of the invention was relatively low.

For example, 24 hours of treatment with positive silver ions produced modified cells only in a zone 1 cm wide around the anode, whereas in example I, supra, the same procedure changed substantially all the 3T6 cells in the chamber.

EXAMPLE IV.

Figure 6:
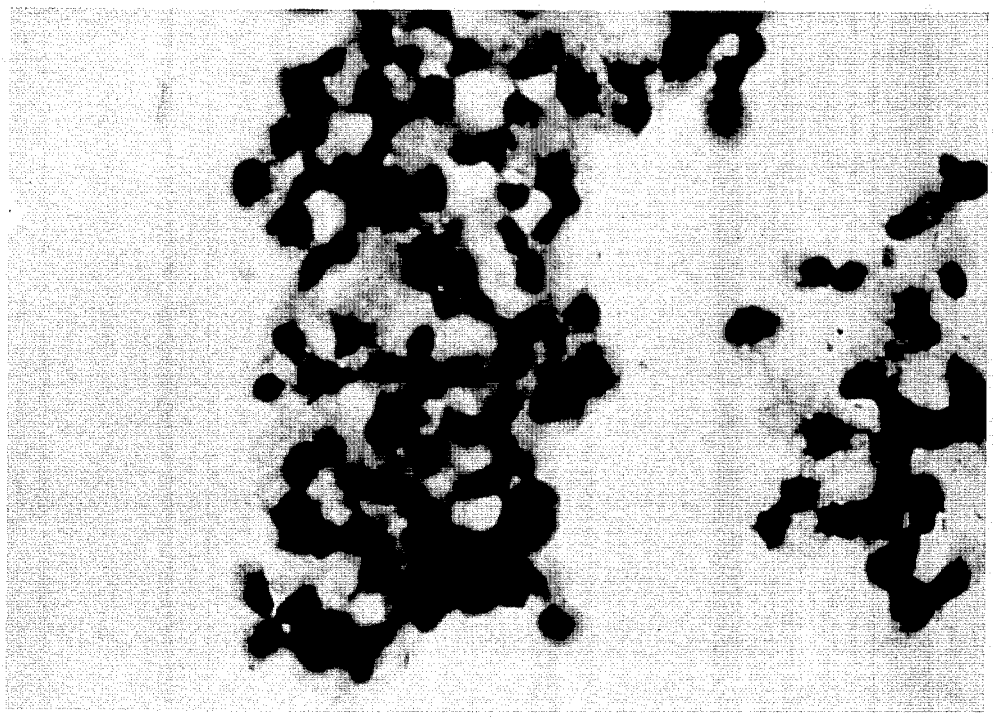
FIGS. 6 and 7 are microphotographs of stained cultures of human fibrosarcoma, showing the effect of the invention.
Figure 7:
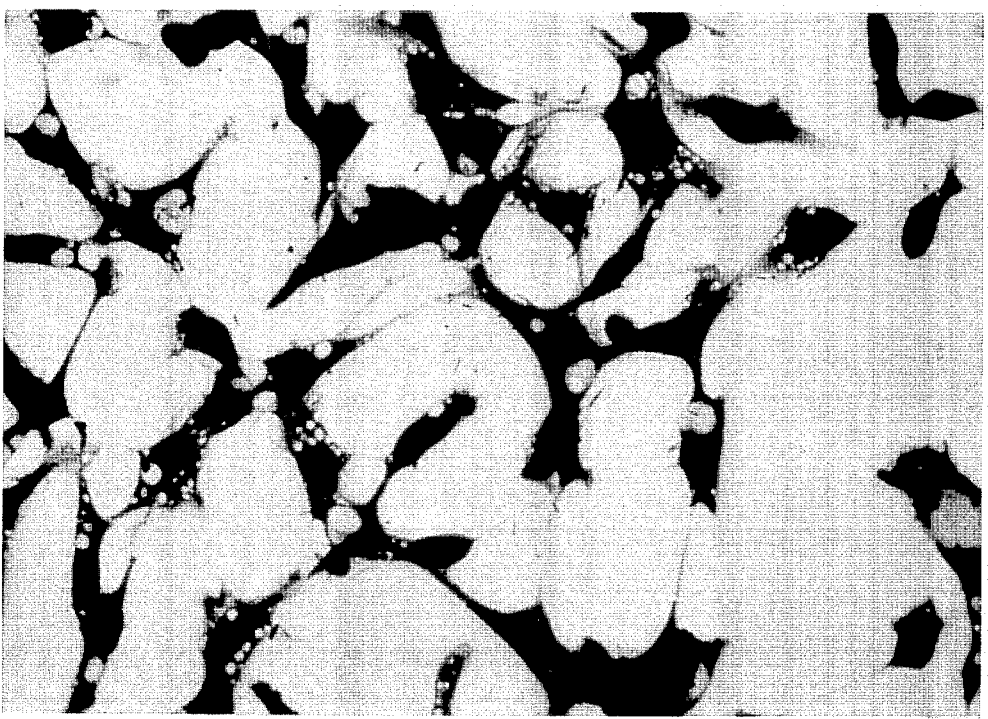

Modifying malignant cells (human fibrosarcoma ATCC CCL 121, HT 1080). The modification procedure is as in I, supra, and in addition some HT 1080 was subjected to negative low intensity direct current via a silver electrode. Here, the positive silver ion treatment caused the usual round cell populations to result, these being stable and having no mitotic activity unless removed, as before, to a silver-free medium, where they reverted to the original malignant form, after a long delay, 2-4 times longer than required by the normal cells of Example I. On the other hand, low intensity direct current treatment appeared to cause the malignant cells to proliferate at an increased rate without, however, changing their form. These results are shown in FIGS. 6 and 7, which show a vast difference in appearance between the modified cancer cells and the unmodified cancer cells. Thus, FIG. 6 is a microphotograph of Wright-Giemsa stained cancer cells after 24 hours of electrical application thereto of positive silver ions. Interestingly, FIG. 7, which actually shows what happens when the silver electrode 7 is made the cathode and the cancer cells in chamber 5, (FIG. 1), are subjected to low intensity direct current for 24 hours, also fairly illustrates what the original cancer cells looked like before modification by positive silver ions. While it is not immediately evident from FIGS. 6 and 7, examination of the results of anodic and cathodic treatment of the cancer cells, as well as comparison with the untreated cancer cells, indicates that the cathodic treatment encourages proliferation of the cancer cells.

EXAMPLE V.

Figure 8:
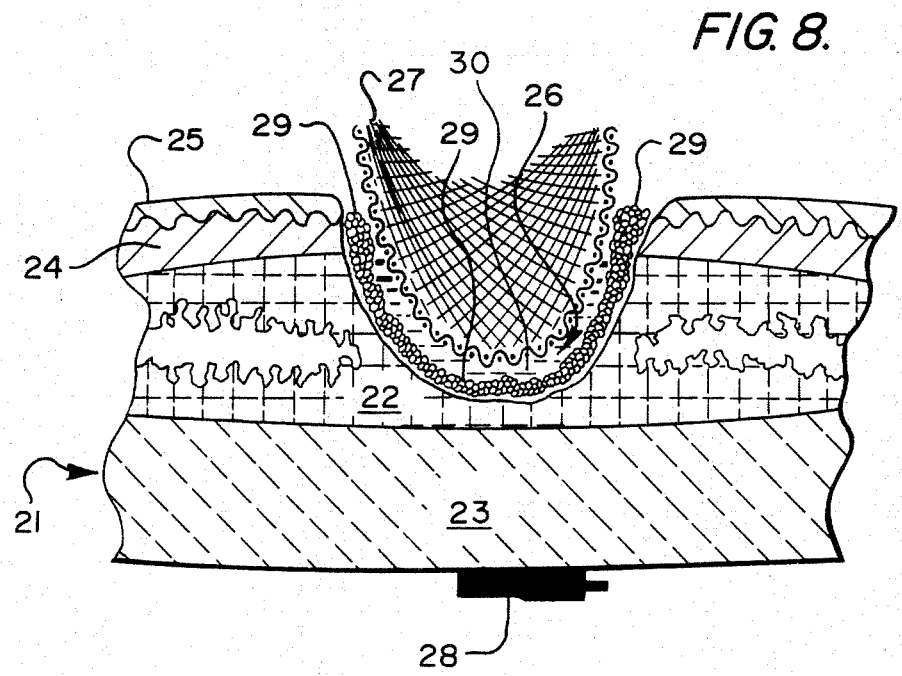
FIG. 8 is a drawing showing apparatus arranged to expose living cells, in situ at an in vivo lesion, to anodal metal ions, in accordance with the invention.

Healing bone lesions. In FIG. 8, a lower portion 21 of the leg of a live human being is portrayed in longitudinal section through the tibia 22, which is, of course, substantially surrounded by soft tissue 23 enveloped in somewhat exaggeratedly-shown sub cutis 24 and skin 25. An osteomyelitic lesion 26 is also shown as having gone nearly all the way through the tibia, and as erupting through sub cutis and skin as well.

In order to heal the lesion, I apply a sheet electrode 27 of flexible silver nylon mesh to the surface of the lesion, so that it is at least approximately in contact with most or all the exposed surface of the lesion. In order to assure electrical transfer of silver ions to the lesion, the surface of the lesion and the mesh are wetted with saline solution whereby any gap between lesion surface and mesh is bridged by saline solution. The silver mesh is conventional and has been used, prior to my invention, for obtaining bactericidal effects due to the silver.

Figure 11:
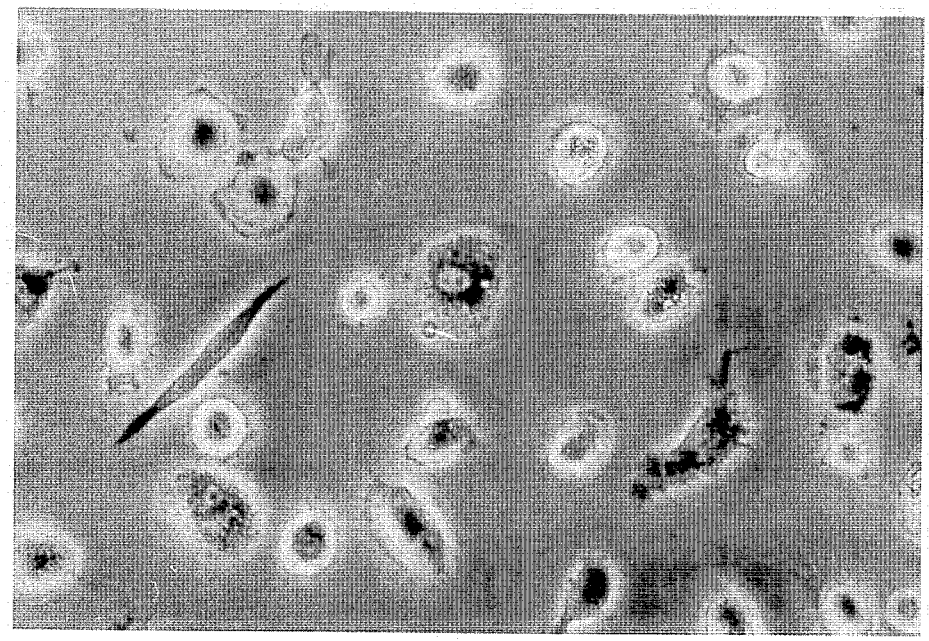

A carbon electrode 28 is secured to the skin surface opposite the sheet electrode 27, and an LIDC generator (not shown in FIG. 11 but preferably such as the one indicated, supra, in example I is connected to the sheet electrode 27 and the electrode 28 such as to make these respectively anode and cathode when the greater is turned on, sheet electrode 27 typically being made 0.9 volt positive to electrode 28, providing a current in the range 1-2 microamperes per square centimeter of the interface of sheet electrode 27 with the lesion 26. It is to be noted that the material of electrode 28 has no effect on what is occurring in the lesion. The silver ions do not penetrate the tissue at electrode 27 deeper than about 1 centimeter, so the electrical coupling between electrodes 27 and 28 is purely electronic. It is to be noted that ions injected into the tissue or culture medium do form compounds therewith. Thus, the positive silver ions bind to protein, etc., so presumably only some of the amount of injected ion is available for cell-modification, and/or some initial capacity for binding ions may need to be satisfied before any ion becomes available for cell modification. In any event there seems to be some storage of ion in silver-treated culture or tissue, since the silver effect persists for some time after the source of silver is removed.

Typically, maintaining this current, as is known, substantially continuously for approximately a week, causes bacteria counts, as measured, in samples of wound material taken at the times of routine dressing thereof, (e.g., daily) to drop to practically zero. By the third or fourth day, the bacteria count usually goes below a clinically zero level, free pus and necrotic tissue are no longer present, and granulation tissue growth can be seen to have begun. For example, Becker et al., above-cited, use this disinfection procedure as a necessary preliminary to cathodic stimulation of bone growth in the lesion.

According to my invention, however, after such disinfecting, I continue to apply silver ions to the lesion using a positive silver electrode in order to enhance the natural healing process therein and, as well, to keep the lesion in the disinfected state. Thus, at the point where Becker et al, to stimulate bone growth, reverse the polarity, I instead keep sheet electrode 27 positive, and, in order to enhance healing, now extend the positive silver ion treatment of the lesion so long that the total time of positive silver ion treatment is far in excess of the time Becker et al use it for initial disinfection purposes. The treatment is continued until the wound can be easily treated by conventional methods.

Early in the extended phase of the positive silver ion treatment a thin, scant whitish exudate 29 begins to appear between the sheet electrode 27 and the adjacent surface of lesion 26, (the showing of the exudate, and the spacing between sheet electrode 27 and lesion surface are exaggerated in FIG. 11, for clarity).

About the sixth or seventh day of continuous silver anode treatment, the exudate thickens, becomes yellowish-white more copious and is non-odorous—up to 5 cc can be collected from under 50 $cm^2$ of surface of sheet electrode 27.

Heretofore, an exudate of this sort would expectably be a mere reactive substance composed primarily of eosinophil and polymorphonuclear white blood cells. However, in the present case, entirely unexpectedly, but like in Example I, supra, the exudate under positive silver ion treatment closely resembles active hematopoietic bone marrow, except that there is present in the exudate nothing resembling megakaryocytic precursors of blood platelets. Also, there is an unexpectedly rapid growth of granulation tissue beneath the exudate, marking an obvious acceleration of healing in these treated wounds.

Practice of my invention results in exudate of this sort appearing even in lesions due to adult-type osteomyelitis of long bones of the extremities, where active marrow would not normally be present. Again, even the possibility that the treatment had stimulated residual fibro-adipose marrow cells at the site of the lesion can be ruled out, since, due to patient age (advanced) and effective sclerotic obliteration of the bone marrow cavity, there should have been no marrow cells of any kind accessible to the effect of treatment according to my invention.

However, according to my investigation, what appears to be occurring is that soft tissue fibroblasts, i.e., mesenchymatous cells which normally give rise to connective tissue, are being transformed into viable less-differentiated cells, very much like hematopoietic cells. In other words, by applying positive silver ions, long enough and in a suitable range of direct current density, to in vivo lesions containing bone, flesh, blood and the expectable disease concomitant matter: pus, microorganisms, cell debris, etc., I not only destroy microorganisms with the silver ions, but next thereby dedifferentiate living fibroblasts, at the site of the lesion, to primitive cells, in effect, thereby artificially producing a blastema (the aforesaid exudate in the bone lesion) from which regeneration of bone and soft tissue occurs.

EXAMPLE VI.

Modifying normal human fibroblasts obtained from granulation tissue. The blastemic nature of the material in lesions treated in accordance with Example V, is indicated by culturing a small specimen of granulation tissue (a loose aggregate of fibroblasts and capillaries which is the normal healing tissue in open wounds), which was obtained from the wounds of a patient, under my novel low intensity direct current silver ion healing therapy in accordance with Example V, supra. The granulation tissue in these wounds grows very rapidly and abundantly while it presumably produces the above-described cellular exudate. If granulation tissue is taken from a normal wound, not treated with silver, it will produce a few fibroblasts, in culture, at a very slow rate which is normal for normal cells that are not malignant or transformed.

Figure 9:
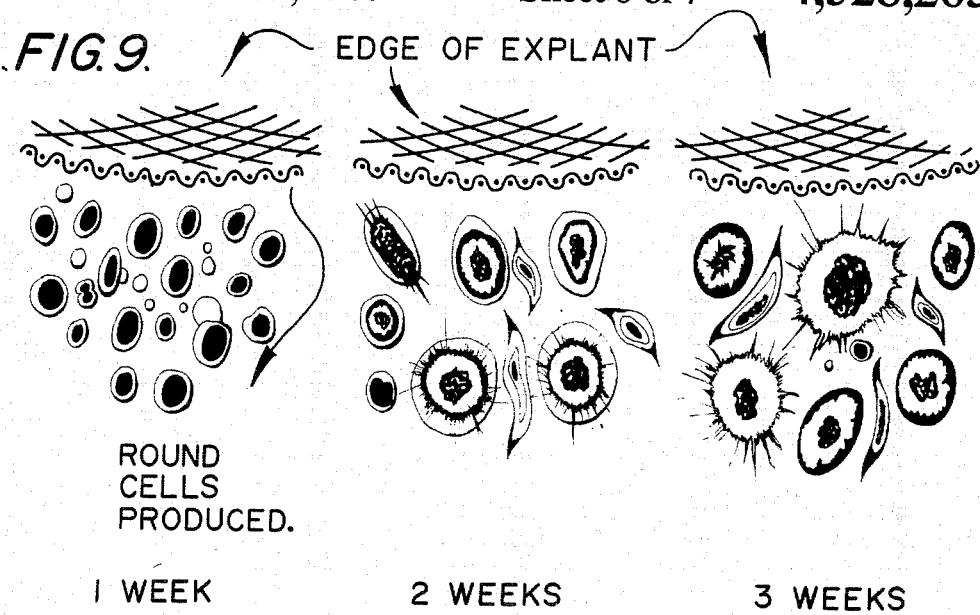
FIG. 9 is a drawing showing a set of cell morphology changes, produced in a sample of explanted tissue in accordance with the invention, FIGS. 10, 11 and 12 being phase contrast microphotographs showing actual live cell structure corresponding to FIG. 9.

Thus, small granulation tissue specimens of 1-2 mm diameter excised by scalpel at the time of dressing change and placed immediately in several changes of culture media to wash off exudate cells, were then placed on microscope cover glasses in culture medium (N.B., in the absence of silver), and examined under the microscope. This microscopic examination revealed an almost exclusively fibroblast population, whereas very few exudate cells were seen, and the only "free" cells in the culture were a few erythrocytes drained from the capillary network. Within 2-3 days an abundant cellular outgrowth was seen microscopically. As shown in FIG. 9, this consisted of the small round cell, the type also most frequently seen in Zone II of FIG. 2. FIG. 9 also shows that, by the end of one week of treatment, the free cell population was abundant and there were now evidences of mitotic activity in this free cell population (therefore these cells were not produced by the granulation tissue only). No fibroblasts were seen at this time. The difference, compared with wounds not treated with silver, is striking.

By two weeks (FIG. 9 again) a pleomorphic appearance of the free cells was noted, with many large round cells. There were many cells with irregular cell outlines that may have been amoeboid, and a few fibroblasts now made their appearance. By the third week (FIG. 9) the cover glass was covered with a pseudotissue of fibroblast strands separating islands of pleomorphic round cells. Many of the pleomorphic cells had become enormous in size. Wright-Giemsa stains of all of these cells from the first week to the third demonstrated a population of extremely active cells, many appreciably engaging in quite unique activities. For example, filapodia formation was common, but seemed to be serving as an intercellular communication mechanism. The giant mononuclear cells seemed to be receiving "donations" of nuclei from the smaller round cells. Taken all together, the only similar tissue observable in nature would be the early stage limb blastema in animals, such as the salamander.

Figure 10:
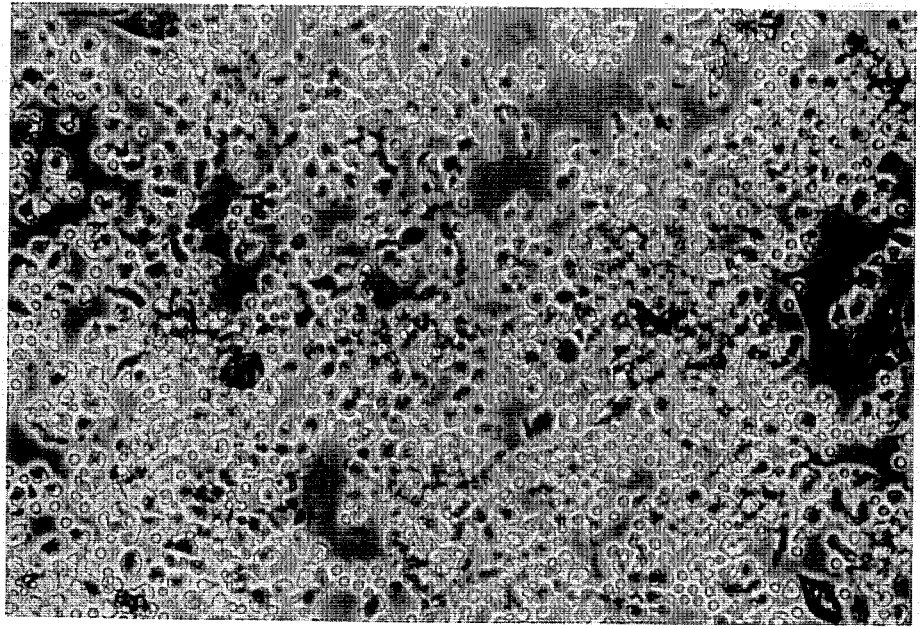
Figure 13:
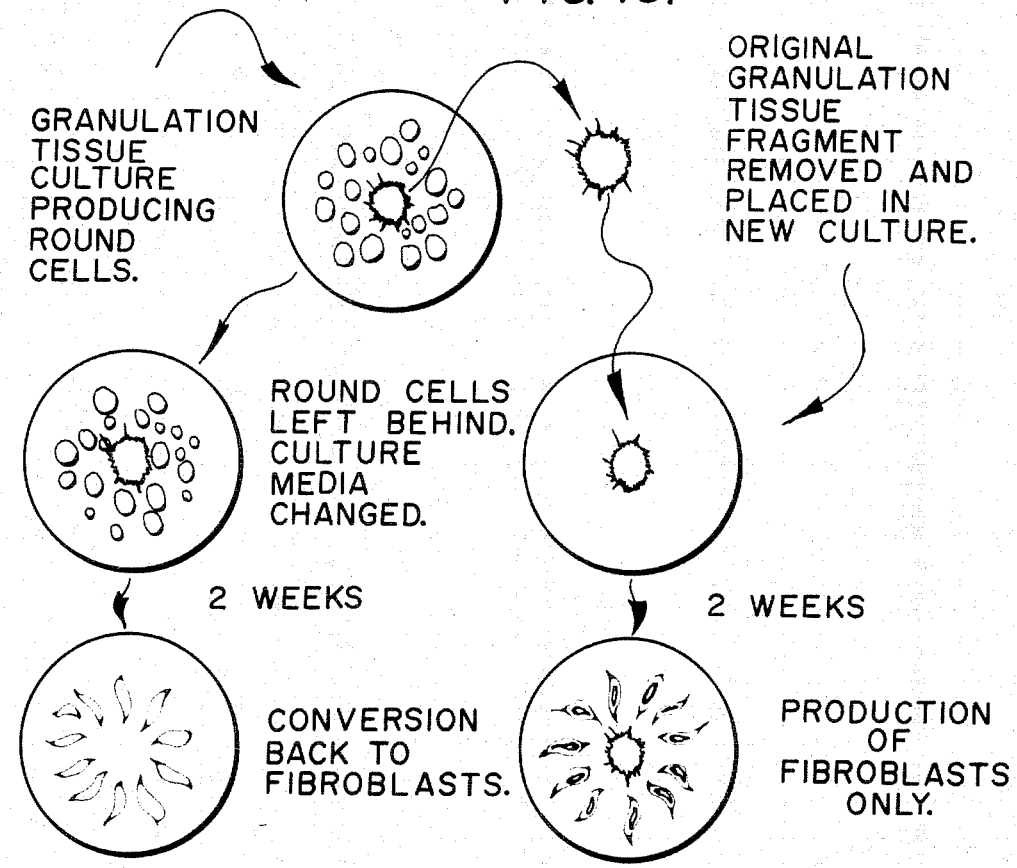
FIG. 13 shows a further set of cell morphology changes, in accordance with the invention.
Figure 12:
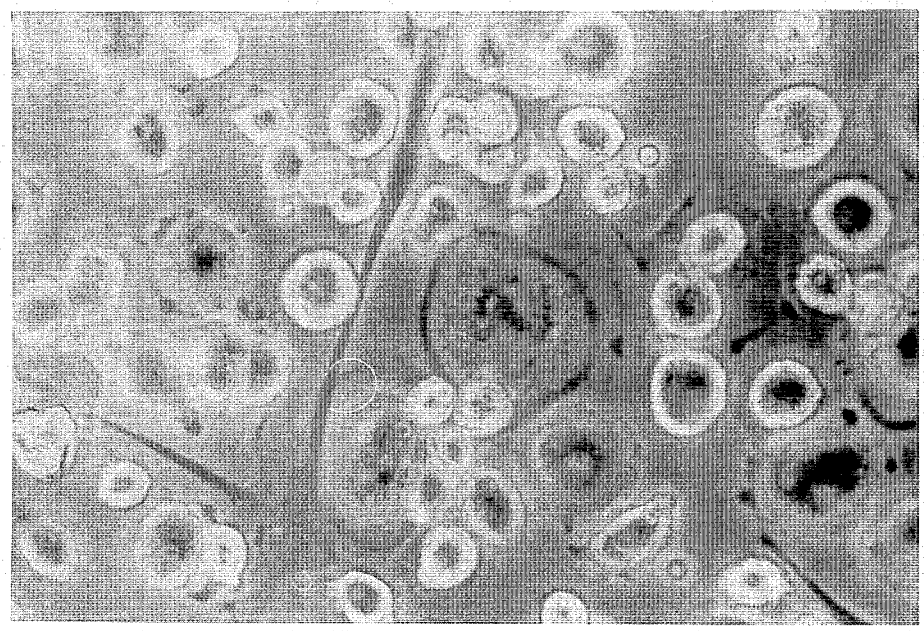

Comparison of phase contrast microphotographic FIGS. 10, 11 and 12, which respectively correspond to the stages of FIG. 9, with FIGS. 3, 4, and 5, shows that the overall cell populations of these three series greatly resemble one another. In any event, in Example VI, the changes in culture persist and the unusual round cells continue to multiply even after three weeks of culturing. However, by the fourth week, the fibroblast population is noted to be increasing. These fibroblasts, which are entirely normal in appearance, are being largely produced by the round cell population, as is shown by taking a granulation tissue culture that is at the end of the second week stage of this example, removing the granulation tissue explant, and placing it in a separate culture with silver-free media at the same time. The remainder of the original culture, which now consists of round cells with a very sparse fibroblast population, is continued in culture but after a similar change to silver-free media. By the end of the third week, the original granulation tissue explant will be producing a pure fibroblast outgrowth at a slow rate, whereas the round cell population now will have become almost 100% fibroblast. (FIG. 13 is a self-explanatory graphic description of the foregoing scheme).

The aforementioned results indicate that the original explant of granulation tissue from the treated patient contained silver ions. These silver ions are washed out with the every two-day change of culture medium and by the end of the second or third week are essentially gone from the preparation. The cell changes then cease and the fibroblasts of the explant produce typical fibroblats at a very slow normal rate. It is simiarly apparent that, if the silver treatment were continued through this time as in example 1, the explanted tissue could be induced to continue to produce these cells indefinitely.

The foregoing results mean to me that the electrically generated silver ion produces a transformation of tissue fibroblasts into relatively primitive cells resembling and possibly functioning like primitive cell types, e.g., hematopoietic marrow. The change, however, is neither permanent nor malignant, since with continued culture in silver free media, these same cells still revert to fibroblasts. (It must be kept in mind, also, that such a fibroblast reversion would be a normal process in hematopoietic marrow in vitro.) In any event, a number of clinical applications appear possible.

1. The ability to dedifferentiate normal cells, either in vivo or in vitro could lead to blastema formation in the human body and subsequent regeneration of many organs and tissues. Thus, granulation tissue technique described above appears to produce a rapidly growing multipotent tissue that might serve as a blastema for human tissue regeneration. Therefore, on the basis of excellent results reported for implanting or injecting small aliquots of hematopoietic marrow into gingival defects, I believe that direct silver anode stimulation of the fibroblastic cells of the gingva would result in regeneration of the gingiva itself. Again, muscle fibroblasts could be induced to dedifferentiate in vivo by this technique and then redifferentiate into muscle if placed in situ in the original muscle. In this way, necrosed areas of myocardial infarct would be replaced. Indeed, it is possible that resecting a population of fibroblasts from a patient and treating it in vitro with Ag+ ion technique would produce a population of multipotent cells, which, if surgically or by injection introduced into areas of a single tissue type, would simultaneously regenerate, aid in healing of, or protect from infection any or every desired part, organ or sort of tissue: liver, kidney, heart muscle, etc.

Again, by adding suitable inducers to in vitro populations of dedifferentiated cells, different tissues parts, or even organs could be created. For example, a powdered form of bone collagen is known which, if implanted in bone lesions, can result in bone growth there, and if implanted in soft tissue (muscle) can result in bone growth there. It has also been claimed that treated skeletal muscle can induce heathly cardiac muscle growth. See Polezhaev, L. V. "Organ Regeneration in Animals", publ. C. C. Thomas, Springfield, Ill. 1972 (pp. 119–122).

2. Treatment of cancer. In the changed state, (Example IV) malignant cels might be more sensitive or vulnerable to chemotherapy or radiation. Again, the fact that modified cancer cells take some time to revert to their malignant form is in the nature of a remission, and, moreover, continuous or periodic silver treatment in vivo could apparently extend that time indefinitely. In other words, the tumor-cell population would be stabilized, which would give normal healing processes the opportunity to destroy tumor cells faster than they can be produced, and/or to supplant them with normal cells. If it turns out that the silver treatment changes the malignant cells to truly dedifferentiated or multipotent cells, they would then be subject to normal biological control or induction mechanisms which would cause them to redifferentiate to their original, non-malignant, specialized type.

3. Fibrotic cells in the marrow of patients with myelofibrosis or having radiation exposure, could be transformed into functioning, blood forming, hematopoietic marrow.

4. In cases of radiation overdose, the silver anode might be useful in areas of soft tissue radiation necrosis, not to stimulate hematopoiesis, but to provide a population of multipotent cells to assist in healing.

5. Some agents used in cancer chemotherapy are very damaging to hematopoietic marrow, by producing anemia or leukopenia. Their utility might be extended by marrow stimulation with silver anodes, which would encourage hematopoietic cell production.

6. It should be possible to secure fibroblast cultures that could be frozen and stored in the case of workers at high risk of radiation exposure. In the event of accident, the cultures could be activated, treated with Ag+, and the resultant zone II cells harvested and used as marrow transfusions.

7. Improved possibilities for production of biochemicals also present themselves. Thus, in the case of fibroblasts which result by redifferentiation of round cell population cultured in Ag+ free media, in accordance with the scheme of FIG. 13, these can be caused to produce an interferon. While at first sight, this might seem like a rather modest result, it is to be observed that the dedifferentiation/redifferentiation process has produced a fibroblast cell line that reproduces at a greater rate than the fibroblast line of its ancestral source—the granulation tissue explant. One obvious way of utilizing this in vitro production of interferon is harvesting and fractionation. Another use, however, would be to reimplant the redifferentiated cell line into the donor, in order to enhance endogenous interferon production. The culture could also be stored for furture use of the donor.

It will be remembered that, under the best of prior art circumstances, human cell lines multiply slowly. However, as Example VI show, the production of round cells, due to the silver treatment, is quite rapid, and therefore, even though it takes about three weeks in silver-free medium for the round cells to revert to fibroblasts, the effective rate of fibroblast production is higher than had one started with equivalent quanitities of fibroblasts and attempted to multiply them over the time required to culture and treat granulation tissues to get round cells for reversion to fibroblasts.

Presently, biochemical production by microorganisms and cells frequently involves intrinsically or potentially hazardous expedients. Thus, one modifies a bacterium with viral genetic material, or hybridizes normal and cancerous cells. In contrast, my inventive technique of dedifferentiation, which provides possible multipotent cells, creates the possibility of respecializing those cells along lines which will result in cells which produce, or can be caused to produce, desired biochemicals of kinds endogenous to the source of the original cells, e.g., hormones such as insulin.

Some hypotheses as to the effect of electrically driven, positive silver ions have been tested cytochemically. One is that such treatment merely changes the form and size of the fibroblasts, that is to say, they remain fibroblasts in nature. If so, it can then be said that while the immediate effect of the treatment is morphological, the overall effect is to repress mitosis and perhaps even metabolic activities. Thus, as Example VI shows, in the absence of the LIDC, but in the presence of silver, the round cell population remains static, changing neither in number nor form nor nature, until removed to a silver-free medium, whereupon they revert to fibroblasts of normal shape and function.

On the other hand, if the hypothesis is that the primitive cells are of a hematopoietic nature, it should be possible to detect the presence of myeloid, monocytic and or lymphoid cells by testing with staining agents known to be able to differentiate among these types of cells. Accordingly, over a period of some months, in one calendar year, and using modified cells of Example I, test stains were run, as follows:

TABLE I

| | Percentage Staining | | | |
|---|---|---|---|---|
| Month, Day | Staining Agent | Chamber 5 | Chamber 4 | Chamber 4a |
| 3/25 | Alpha naphthal acetate esterase | 0% | 0% | 0.5% |
| 3/25 | Peroxidase | 1% | 0% | 0% |
| 3/31 | Sudan black B | 17% | 10% | 6% |
| 3/31 | Wright-Giemsa | | | |
| 4/22 | Beta-glucuronidase | 0% | 0% | 0% |
| 4/22 | Periodic acid schiff | 33% | 64% | 81% |
| 4/28 | Alpha naphthal butyrate esterase | 0% | 0% | 0% |
| 4/28 | Alpha naphthal acetate esterase | 0% | 0% | 0% |
| 5/5 | Acid phosphatase | 0% | 2% | 0% |
| 5/22 | Peroxidase | 2% | 0% | 0% |

TABLE I-continued

| | | Percentage Staining | | |
| --- | --- | --- | --- | --- |
| Month, Day | Staining Agent | Chamber 5 | Chamber 4 | Chamber 4a |
| 6/5 | Periodic acid schiff | 57% | 78% | 52% |
| 6/5 | Sudan black B | 37% | 14% | 33% |
| 8/26 | Chloroacetate esterase | 0% | 0% | 0% |

Table I, supra, is mainly self-explanatory. The "Percentage Staining" figures are based on counting the number of stained cells per 200 cells per sample. The "Chamber" designations indicate the sample treatment, namely, the "Chamber 5" column Example I's positive silver ion low intensity current treatment in chamber 5, whereas "chamber 4? and "chamber 4a" represent Example I's controls using low intensity direct current silver cathode, and currentless contact with silver, respectively.

While a few samples were tested at what corresponds to the six hour point of the Example I protocol, the rest were tested at the 24 hour point thereof. A number of cultures were used, several samples being taken from each other.

No entry of percentages was made for Wright-Giemsa because it is known to be non-selective.

In my view, the results shown in Table I are inconclusive as to the above-stated hypotheses, because no pattern of selectivity is evident therefrom. However, Table I is consistent with the hypothesis that the round cells are neither fibroblast nor hematopoietic. As it happens, the visible yield of round cells, in example I, is relatively scant, so it may be that there are simply not enough round cells present to give a definite pattern of selectivity.

While the fundamental aspect of my invention is the electrical application of positive silver ions to cells, such as to modify or dedifferentiate them, the uses thereof which I have disclosed or proposed, supra, do not necessarily depend on the particular agent disclosed herein as causing modification or dedifferentiation. Accordingly, none of the claims infra is to be construed as restricted to silver, unless silver is specifically set forth therein or in a claim on which it is dependent. Nonetheless, it needs to be kept in mind that in the context of the present invention, silver appears to be unique in that it is not cytotoxic, not carcinogenic, not mutagenic, and not harmful to tissue, but is nonetheless and simultaneously a destroyer of bacteria, fungi, and other microorganism, a dedifferentiating agent, and a growth promoting agent for mammalian cells.

In addition to silver, I have cultured 3T6 fibroblasts in contact with wires made of metal other than silver. Thus, nickel, palladium, copper, tin, zinc, cobalt and cadmium were tested. No other metal had the characteristics of silver, and while some, such as cobalt and zinc, produced some similar changes, they also killed may cells. No electricity was used in these tests, however.

In one test series, nickel, palladium, copper, tin, zinc, cadmium, zinc and cobalt wire were added, separately, to seedings of 3T6 fibroblasts, which were then cultured as during the first 72 hours of the protocol of Example I, supra. Nickel and palladium wires appeared to have no effect, whereas copper and tin wires appeared only to cause formation of blebs and filapodia in cells in the immediate vicinity of the wires. Zinc and cadmium wires altered the appearance of the entire culture, producing many free-floating, basophilic, small, round cells, and many non-viable cells. Cobalt wire gave similar results, but with a greater proportion of viable cells, and, in addition, many binucleate cells made their appearance.

In another series of tests, 3T6 fibroblast cultures were seeded and grown for 48 hours in an incubator. Cobalt, cadmium, zinc and iron wires were than added, separately, to the cultures, which were then incubated for 24 hours. In this series, cobalt and zinc wires had the same effect, as before, except that now the changes were limited to the immediate vicinity of the wires. Also, here the cobalt wire appeared to cause the appearance of many cells like those of Zone I, FIG. 2, and there was a sharp boundary between the changed and the unchanged parts of the culture. In the use of zinc, the was no sharp boundary between the changed cells and the rest of the culture. Unlike the zinc and cobalt wire, the cadmium wires effect again appeared to pervade the whole culture, producing both very small round cells and many non-viable cells. The culture with iron wire showed some bleb formation, but no round cells, or free floating cells, and except for iron oxide in cells in the immediate vicinity of the iron wire, the remainder of the culture remained normal.

Unlike the case of silver, in some cases the two test series showed cytotoxic effects. This does not necessarily exclude metals causing those effects from utility in cell-modification, however, and in fact, zinc is used in dermatological preparations, and cobalt in orthopedic prostheses. However, I would exclude cadmium, in view of its known toxicity and reactiveness as shown by its capacity for whole-culture effects even in the incubation test where the cells were not exposed to metal until after they had gone through their growth phase.

As the net result of the foregoing tests, I believe that cobalt and zinc would be useful for cell modification when used as anodes, namely, as sources of electrically driven positive ions to be applied to the cells, much as in the case of silver. Both cobalt and zinc are more reactive than silver, and so might therefore have to be used with lower currents and voltages. Also, since cobalt is known to be growth-enhancing for bacteria, it lacks the versatility of silver which disinfects lesions, as well as modifies cells, when used as an anode.

The test appear to me to rule out the possibility of palladium and nickel having cell-changing properties of any kind. Iron may be ruled out for a similar reason, and also because of the oxide deposition in nearby cells. Cadmium appears to be too cytotoxic, although quite active. Even so, it should be noted that toxicity, as such, does not prevent pharmacological agents from being used therapeutically.

I claim:

1. A cell modification process which comprises the steps of:
    (a) providing an element of metal at a culture medium having cells of a mammal therein including transformable cells chosen from the group consisting of fibroblast cells and malignant cells;
    (b) causing the element to introduce ions of the metal to the medium, the ions being substantially free of anions;
    (c) contacting the cells with the ions;
    (d) maintaining said contact for a sufficient period of time and with a sufficient amount of the ions to change the transformable cells to unspecialized cells characterized by their relatively multi-potent state; said period of time being greater than the time normally necessary to inhibit or render bacteriostatic bacteria in a wound with respect to fibroblast cells, and being less than the time normally necessary to kill Erlich's ascites fluid tumor cells with respect to free-floating malignant cells;

(e) permitting or inducing a desired number of unspecialized cells to redifferentiate into cells of the culture medium other than fibroblast cells or malignant cells.

2. The cell modification process of claim 1 wherein the element of metal consists essentially of silver.

3. The cell modification process of claim 1 wherein the element of metal is connected to an anode of a source of direct current, and the medium is connected to a the cathode thereof.

4. The cell modification process of any one of claims 1 through 3, wherein the cells are situated on a substrate of collagen.

5. The cell modification process of any one of claims 1 through 3 wherein the transformable cells are fibroblast cells contained in mammalian granulation tissue.

6. The cell modification process according to any one of claims 1-3 wherein the culture medium is a lesion in a mammal.

7. The cell modification process according to any one of claims 1-3 wherein the culture medium is a tumor in a mammal.

8. An unspecialized cell produced by applying the process of any one of claims 1 through 3 to a fibroblast cell, wherein the unspecialized cell is characterized by its free-floating nature.

9. An unspecialized cell produced according to the process of claim 5, wherein the unspecialized cell is characterized by its free-floating nature.

10. A cell modification process which comprises the steps of:
(a) providing an element of metal consisting essentially of silver which is connected to an anode of a source of direct current and a cathode thereof is connected at a culture medium having cells of a mammal therein including transformable cells chosen from the group consisting of fibroblast cells and malignant cells;
(b) causing the element of metal to introduce ions of the metal to the medium, the ions being substantially free of anions;
(c) contacting the cells with the ions; and
(d) maintaining said contact for a sufficient period of time and with a sufficient amount of the ions to change the cells to unspecialized cells characterized in having a relatively multipotent state; said period of time being greater than the time normally necessary to inhibit or render bacteriostatic bacteria in a wound with respect to fibroblast cells, and being less than the period of time normally necessary to kill Erlich's ascites fluid tumor cells with respect to free-floating malignant cells;
(e) permitting or inducing a desired number of unspecialized cells to redifferentiate into cells of the culture medium other than fibroblast cells or malignant cells.

11. A cell production process which comprises the steps of:

(a) providing an element of metal at a lesion of a mammal, the lesion providing a first culture medium having fibroblast cells of the mammal therein;
(b) causing the element of metal to introduce ions of the metal to the medium, the ions being substantially free of anions;
(c) contacting the cells with the ions;
(d) maintaining said contact for a sufficient period of time and with a sufficient amount of the ions as to cause production, in the lesion, of granulation tissue having fibroblast cells and unspecialized cells characterized by their multipotent state therein; and
(e) introducing an explant of the granulation tissue from the lesion containing fibroblast cells to a second culture medium in the presence of silver ions such that the fibroblast cells produce unspecialized cells at an accelerated rate.

12. The cell production process of claim 11 wherein the element of metal consists essentially of silver.

13. The cell production process of claim 11 wherein the element of metal is connected to the anode of a source of direct current and the first culture medium is connected to the cathode thereof.

14. An unspecialized cell produced by the process of any one of claims 11 through 13, wherein the unspecialized cell is characterized by its free-floating nature.

15. The cell production process of claim 11 wherein the step of introducing an explant of granulation tissue to a second culture medium comprises the steps of:
(a) washing the explant to remove exudate and substantially all unspecialized cells, leaving fibroblasts and
(b) in the presence of the metal ions, allowing the tissue to produce unspecialized cells at an accelerated rate.

16. A cell modification control process which comprises the steps of:
(a) providing an element of metal at a culture medium having cells of a mammal therein chosen from the group consisting of fibroblast cells and malignant cells, the element being connected to an anode of a source of direct current and the medium being connected to a cathode thereof, thereby causing the element to introduce ions of the metal to the medium and into contact with the cells for a sufficient period of time to modify the cells into unspecialized cells characterized by their relatively multipotent state and free-floating nature, the ions being substantially free of anions; said sufficient period of time being greater than the time normally necessary to inhibit or render bacteriostatic bacteria in a wound with respect to fibroblast cells, and being less than the time normally necessary to kill Erlich's ascites fluid tumor cells with respect to free-floating malignant cells; and
(b) thereafter maintaining such modified, unspecialized cells in the medium in the presence of the ions to preserve the modified, unspecialized cells in their modified state.

17. The cell modification control process according to claim 16 wherein the modified cells in their modified state are prevented from proliferating.

18. The cell modification control process according to claim 16 wherein the culture medium is chosen from the group consisting of tumors and lesions.

19. The cell modification control process of any one of claims 16, 17 or 18 wherein the metal is silver.

20. The cell modification control process according to claim 16 which further comprises introducing the maintained unspecialized cells into a third culture medium containing a specific kind of cell and permitting or inducing the unspecialized cells to become redifferentiated into the specific kind of cell other than fibroblast cells or malignant cells.

21. The cell modification process according to claim 20 wherein the third culture medium is in vivo.

22. An unspecialized cell produced by applying the process of claim 16 wherein said unspecialized cell characterized by its free-floating nature is preserved in its modified state.

23. A tissue regeneration process which comprises the steps of:

(a) providing an element of metal at a lesion of a mammal, the lesion providing a first culture medium having fibroblast cells of a mammal therein;

(b) causing the element of metal to introduce ions of the metal to the medium, the ions being substantially free of anions;

(c) contacting the cells with the ions;

(d) maintaining said contact for a sufficient period of time and with a sufficient amount of the ions as to cause production, in the lesion, of granulation tissue having fibroblast cells and unspecialized cells characterized by their multipotent state therein;

(e) introducing an explant of the granulation tissue from the lesion containing fibroblast cells to a second culture medium in the presence of silver ions such that the fibroblast cells produce unspecialized cells at an accelerated rate; and (f) introducing the produced unspecialized cells into a third culture medium containing a specific mammalian tissue composed of a specific kind of cell and permitting or inducing the unspecialized cell to become differentiated into the type of cell that composes the tissue.

24. The tissue regeneration process according to claim 23 wherein the third culture medium is in vivo.

* * * * *

UNITED STATES PATENT AND TRADEMARK OFFICE
CERTIFICATE OF CORRECTION

PATENT NO. : 4,528,265  Page 1 of 3
DATED : July 9, 1985
INVENTOR(S) : Robert O. Becker It is certified that error appears in the above-identified patent and that said Letters Patent is hereby corrected as shown below:

Abstract, line 9, change "hematopoetic" to --hematopoietic--.

Column 1, line 9, change "pharamcological" to --pharmacological--.

Column 1, line 28, change "therea-" to --thera- --.

Column 1, line 57, change "reset of" to --rest of--.

Column 3, line 27, change "the all the" to --all the--.

Column 6, line 55, change "techniques" to --technique--.

Column 7, line 10, change "while" to --white--.

Column 7, line 26, change "reliably" to --reliable--.

Column 7, line 27, change "frequentely" to --frequently--.

Column 7, line 54, change "apparently," to --apparently--.

UNITED STATES PATENT AND TRADEMARK OFFICE
CERTIFICATE OF CORRECTION

PATENT NO. : 4,528,265
DATED : July 9, 1985
INVENTOR(S) : Robert O. Becker

It is certified that error appears in the above-identified patent and that said Letters Patent is hereby corrected as shown below:

Column 8, line 33, change "Example II." to --Example II--.

Column 8, line 64, change "example I" to --Example I--.

Column 10, line 48, change "-white more" to --white, more--.

Column 12, line 42, change "simiarly" to --similarly--.

Column 12, line 44, change "example 1," to --Example I,--.

Column 13, line 14, change "tissues" to --tissue--.

Column 13, line 25, change "cels" to --cells--.

Column 14, line 11, change "show" to --shows--.

Column 14, line 16, change "quanitities" to --quantities--.

Column 15, line 17, change ""chamber 4?" to --"chamber 4"--.

Column 15, line 33, change "example I," to --Example I,--.

UNITED STATES PATENT AND TRADEMARK OFFICE
CERTIFICATE OF CORRECTION

PATENT NO. : 4,528,265

DATED : July 9, 1985

INVENTOR(S) : Robert O. Becker

It is certified that error appears in the above-identified patent and that said Letters Patent is hereby corrected as shown below:

Column 15, line 59, change "may" to --many--.

Column 16, line 17, change "the was" to --there was--.

Column 16, line 47, change "test" to --tests--.

Column 17, line 18, change "to a the cathode" to --to the cathode--.

Signed and Sealed this

Thirty-first Day of December 1985

[SEAL]

Attest:

DONALD J. QUIGG

Attesting Officer

Commissioner of Patents and Trademarks